United States Patent [19]

Matsuno

[11] Patent Number: 5,624,455
[45] Date of Patent: Apr. 29, 1997

[54] FREELY PROJECTABLE/SINKABLE VALVULOTOME AND FREELY PROJECTABLE/SINKABLE VENOUS VALVE VALVULOTOME

[75] Inventor: Kiyotaka Matsuno, Hachioji, Japan

[73] Assignee: Olympus Optical Co., Ltd., Tokyo, Japan

[21] Appl. No.: 549,196

[22] Filed: Oct. 27, 1995

Related U.S. Application Data

[63] Continuation of Ser. No. 299,411, Sep. 1, 1994, abandoned.

[30] Foreign Application Priority Data

Nov. 26, 1993  [JP]  Japan ................................ 5-297061

[51] Int. Cl.⁶ .................................................. A61B 17/32
[52] U.S. Cl. ........................................ 606/159; 606/171
[58] Field of Search ................................ 606/159, 170, 606/171, 180; 604/22

[56] References Cited

U.S. PATENT DOCUMENTS

| | | |
|---|---|---|
| 5,049,154 | 9/1991 | Quadri . |
| 5,234,450 | 8/1993 | Segalowitz et al. ............... 606/159 |
| 5,282,813 | 2/1994 | Redha ................................. 606/159 |
| 5,304,189 | 4/1994 | Goldberg et al. .................. 606/159 |

FOREIGN PATENT DOCUMENTS

| | | |
|---|---|---|
| 4-330767 | 11/1992 | Japan . |
| 8909029 | 10/1989 | WIPO ................................. 606/159 |

*Primary Examiner*—Michael Powell Buiz
*Assistant Examiner*—William Lewis
*Attorney, Agent, or Firm*—Armstrong, Westerman, Hattori, McLeland & Naughton

[57] ABSTRACT

In a valvulotome, when an operating wire is advanced or withdrawn, a pair of arms project from or sink into a sheath, and cutters at the tips or the arms open or close. When the arms are stowed in the sheath, forces causing the two cutters to join change directions sequentially with three pairs of bents of the arms as boundaries. Thus, the blades of the two cutters are stowed in the sheath reliably.

40 Claims, 10 Drawing Sheets

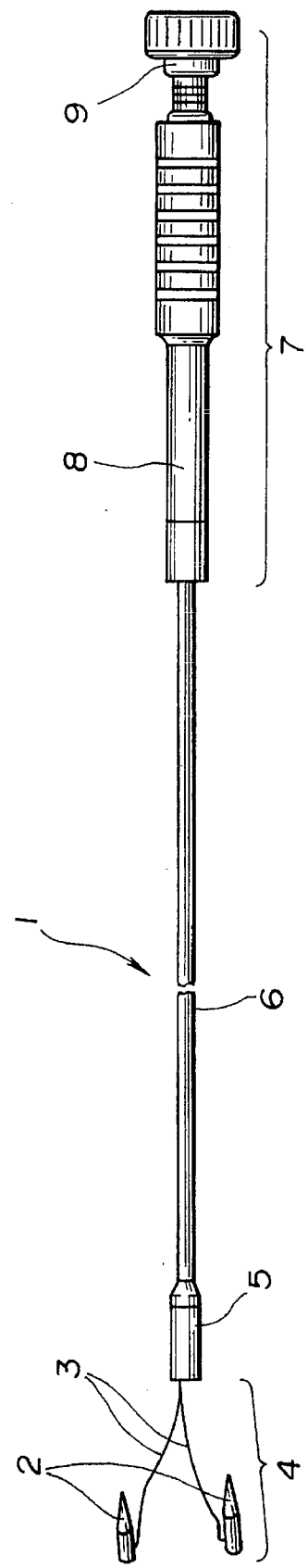

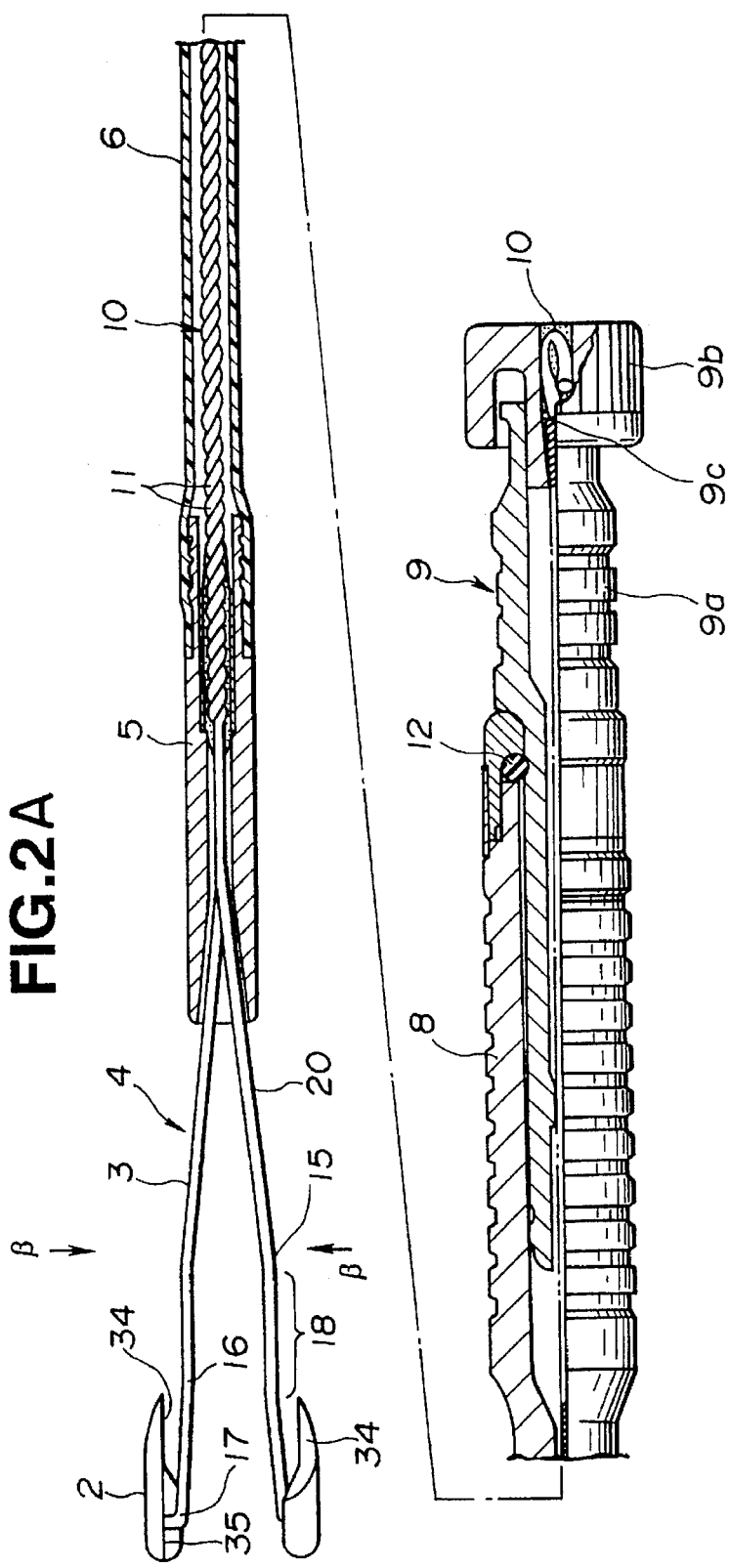
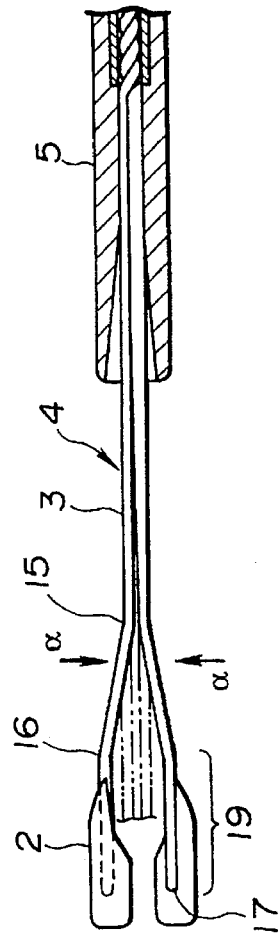
FIG.2A
FIG.2B

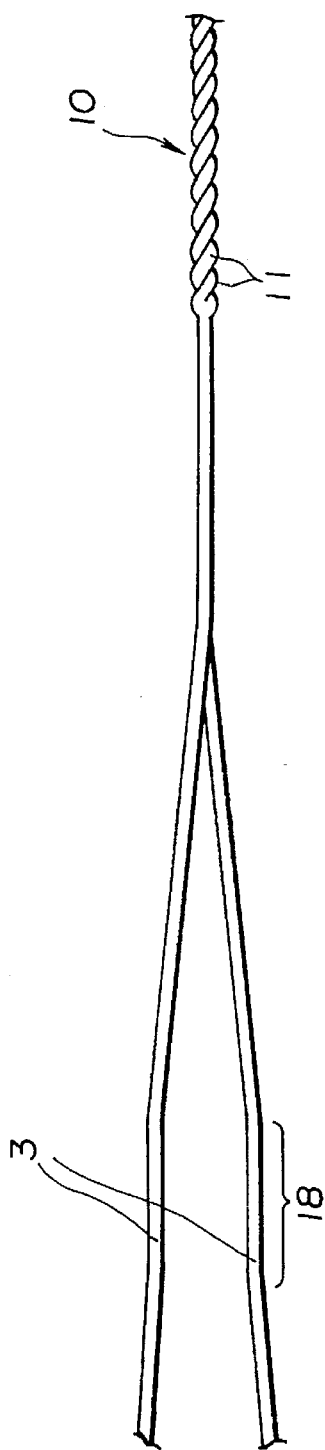
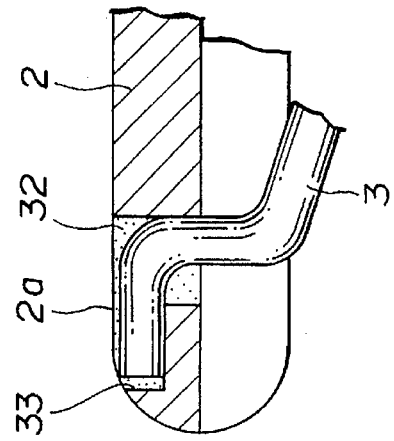
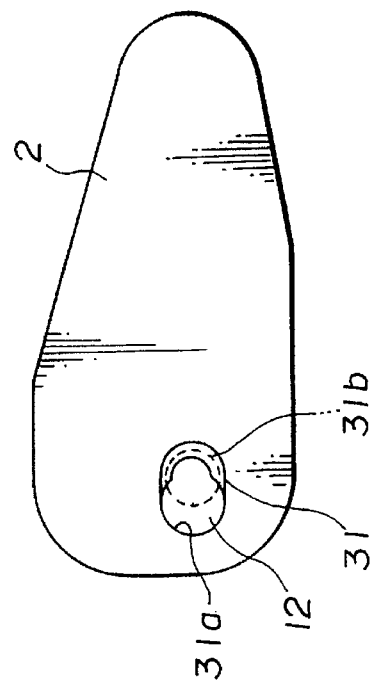
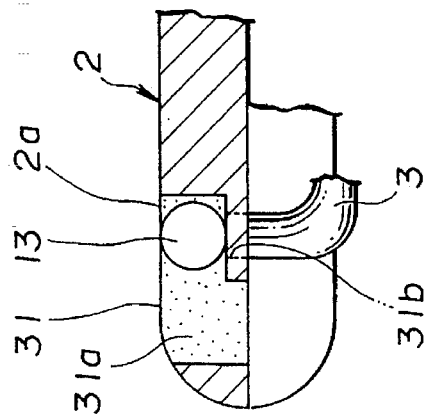

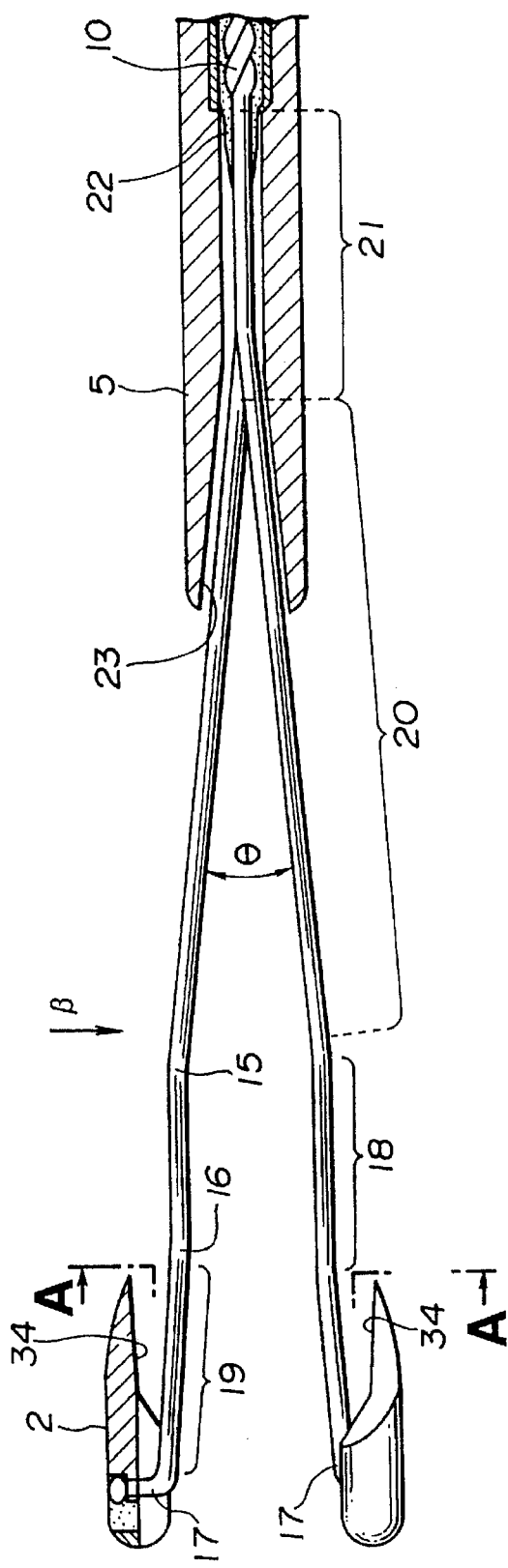

DIRECTION α

DIRECTION β

1

FREELY PROJECTABLE/SINKABLE VALVULOTOME AND FREELY PROJECTABLE/SINKABLE VENOUS VALVE VALVULOTOME

This application is a continuation of application Ser. No. 08/229,411 filed Sep. 1, 1994, now abandoned.

BACKGROUND OF THE INVENTION

1. Field of the Invention

The present invention relates to a freely projectable/sinkable valvulotome for, for example, exsecting a venous valve or the like during angioplasty, including a venous valve valvulotome.

2. Description of the Related Art and Prior Art

For recanalize an artery suffering from insufficient circulation due to arterial obstruction caused by atheroma or thrombus at an inferior ramus of the artery, the obstructed arterial lesion is bypassed using the saphenous vein running in parallel with the artery.

Since the vein used as a bypass has a valve that allows blood to pass in a certain direction alone. Prior to bypassing, the valve must be dissected so that it does not function.

During this kind of surgical procedure, for destroying (resecting) a valve existent in a length of the saphenous vein required as a bypass, an orifice is created at each of superior and inferior regions in a required range, and the vicinities of the orifices are clamped in order to block blood circulation. Thereafter, a valvulotome is inserted through the superior orifice, and an observation means such as a fiberscope is Inserted through the inferior orifice. Thus, valvotomy is undertaken under the direct observation through the observation means.

A prior art is implemented in a device described in U.S. Pat. No. 5,049,154. The device in accordance with the invention has a structure that a pair of cutters arranged symmetrically advance from or withdraw into the tip of a sheath with a certain open width held between them. Blades are formed along the edges of the cutters. FIG. 20 shows the device described in the above patent publication.

As shown in FIG. 20, a working part 62 combined with a distal part 61 of a device body 60 is composed of cutters 63 and arms 64 for supporting the cutters.

The arms 64 have bow-like parts 65 that open out gradually toward the tips thereof so that a certain open width h is ensured with the two cutters 63 open.

The arms 64 have bents 67 so that a gap d is retained between each blade 66 formed along the back edge of each cutter 63 and each arm 64.

Owing to the presence of gaps d, the device can dissect a venous valve by trapping it in the gaps d.

Another prior art described in Japanese Patent Application No. 4-330767 criticizes the device disclosed in the U.S. Pat. No. 5,049,154, pointing out that when the working part 62 is operated repeatedly, the bow-like parts 65 deform. The deformation makes the open width h and gaps d unavailable. Consequently, valvotomy cannot be achieved successfully. The Japanese Patent Application provides an invention below.

The Japanese Patent Application No. 4-330767 has disclosed, as shown in FIG. 21, a venous valve valvulotome comprising cutters 71 having blades 70 along the edges, arms 69 for securing the cutters 71 and forming an operating wire (not shown) located in a proximal portion to be gripped by a user, a sheath 72 that stows the arms 69 and operating wire so that they can advance or withdraw freely. In this venous valve valvulotome, the arms 69 have parallel sections 73 that lie in parallel with the blades 70 of the cutters 71. The arms 69 also have pluralities of bents 74 so that a certain gap is retained between the cutters 71.

The valvulotome disclosed in the U.S. Pat. No. 5,049,154 is not structured so that the cutters can be stowed.

In the valvulotome disclosed in the Japanese Patent Application No. 4-330767, the cutters 71 can be stowed in the sheath 72. The valvulotome therefore offers great safety. The arms 69 are bent so that when the arms 69 with the cutters 71 arranged at the tips thereof are thrust out from the sheath 72, the arms 69 open out. Assuming that the bending angles of the arms 69 differ from a predetermined value, the two cutters 71 may not be stowed in the sheath 72 or the arms 69 may get entangled.

The predetermined value is found in a quite limited range. For bending two blades so that the blades can be pulled into the sheath 72, a skilled worker must repeat fine adjustment many times. The Japanese Patent Application No. 4-330767 has made no particular mention of an arrangement that overcomes this drawback.

OBJECTS AND SUMMARY OF THE INVENTION

An object of the present invention is to provide a freely projectable/sinkable valvulotome and a freely projectable/sinkable venous valve valvulotome each of which can be structured without complexity so that two cutters are stowed in a sheath reliably.

Another object of the present invention is to provide a freely projectable/sinkable valvulotome and a freely projectable/sinkable venous valve valvulotome that even when two cutters are repeatedly stowed in and projected from a sheath, enable easy and reliable stowage of the two cutters in the sheath.

Another object of the present invention is to provide a freely projectable/sinkable valvulotome and a freely projectable/sinkable venous valve valvulotome that even when two cutters are slightly deformed relative to an intended shape, enable easy and reliable stowage of the two cutters in a sheath.

Another object of the present invention is to provide a freely projectable/sinkable valvulotome and a freely projectable/sinkable venous valve valvulotome that enable reliable stowage of at least parts of blades of two cutters in a sheath and thus offer great safety.

According to one preferred embodiment of the present invention, a freely projectable/sinkable valvulotome comprises an armor, an operating wire lying in the armor so as to advance or withdraw freely and having the distal portion thereof bifurcating into two arms, and two cutters attached to the tips of the two arms and provided with blades. The valvulotome is structured so that when the operating wire is advanced or withdrawn, at least parts of the two cutters and the two arms project from or sink into the armor. The two arms of the valvulotome have pluralities of bents so that when the arms are projected, the two cutters open out at a predetermined angle and in different directions. When the arms are stowed in the armor, forces exerted from the armor change directions with the pluralities of bents as boundaries.

Other features and advantages of the present invention will be fully apparent from the detailed description below.

BRIEF DESCRIPTION OF THE DRAWINGS

FIGS. 1 to 15 relate to the first embodiment;

FIG. 1 shows an overall configuration of a valvulotome;

FIG. 2A shows a lateral section of a valvulotome;

FIG. 2B is a arrow-β view of FIG. 2A;

FIG. 3 is a side view showing a structure of arms;

FIG. 4 is a lateral sectional view showing coupling between an arm and a cutter;

FIG. 5 is a top view showing a cutter coupled with an arm;

FIG. 6 is a lateral sectional view showing another structure of an arm and a cutter;

FIG. 7A is a partly sectional view showing a structure of an arm and a cutter;

FIG. 7B is an explanatory diagram concerning stowage of arms;

FIG. 8 is an oblique view showing arms at an angle of about 45° with respect to a direction α or β shown in FIG. 2A or 2B;

FIG. 9 is an oblique view showing arms at an angle of about 45° in a direction different from that in FIG. 8;

FIG. 10 shows an A—A section of FIG. 7A;

FIG. 11 is an explanatory diagram illustrating the usage of a valvulotome;

FIG. 12 is an explanatory diagram illustrating a venous valve valvulotome;

FIG. 14 is a cross sectional view showing the vicinity of a distal part on the scene that arms have just been withdrawn;

FIG. 15 is a top view in which a scene that arms is further withdrawn is seen from the tip of a distal part;

FIG. 16 is a longitudinal sectional view showing a distal part of a valvulotome;

FIG. 17 shows a B—B section of FIG. 16;

FIG. 18 is an arrow-β view of FIG. 16;

DETAILED DESCRIPTION OF THE PREFERRED EMBODIMENTS

Figure 8:
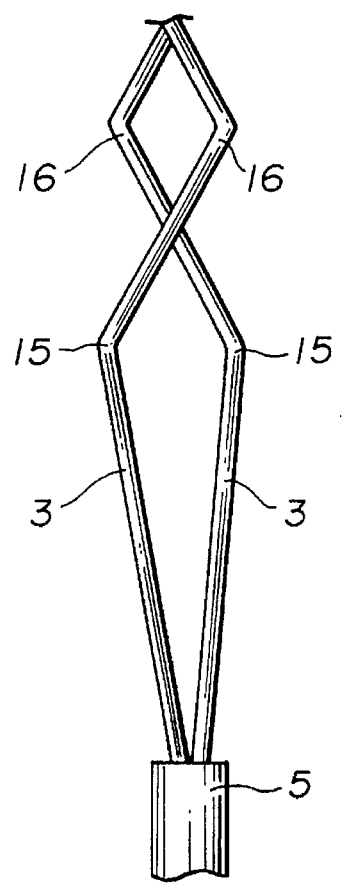
Figure 9:
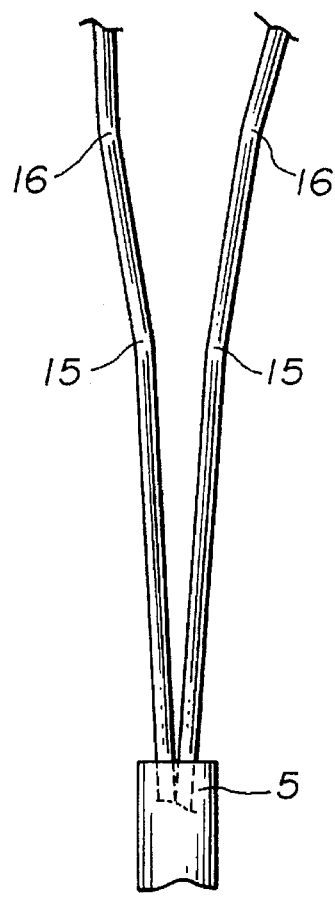
Figure 10:
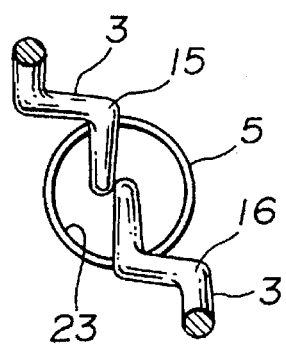
Figure 11:
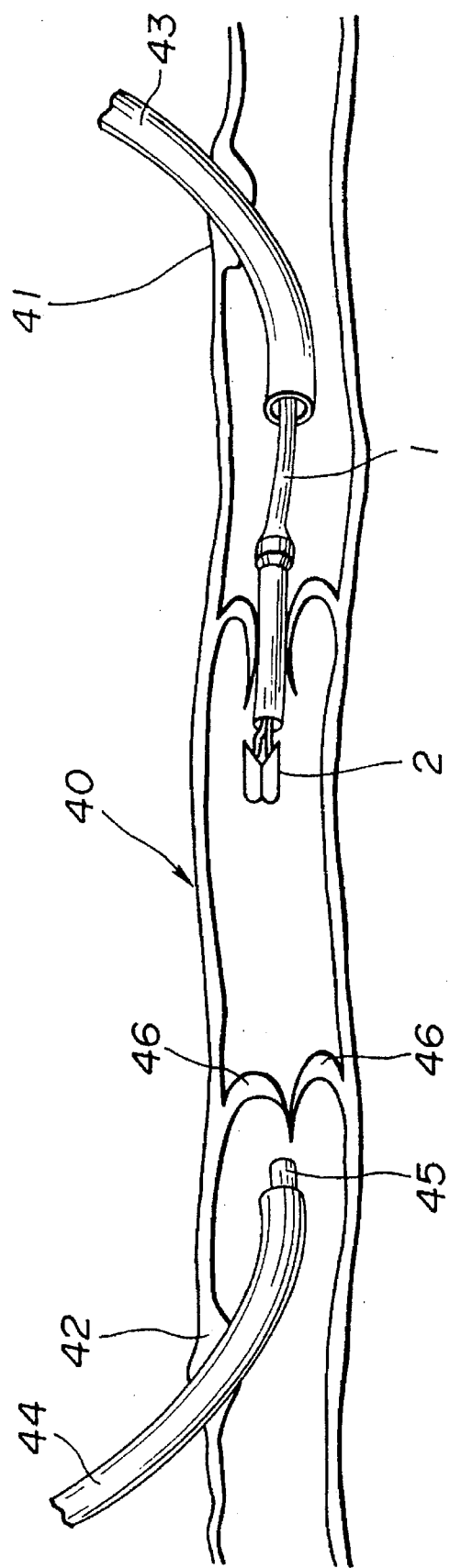
Figure 12:
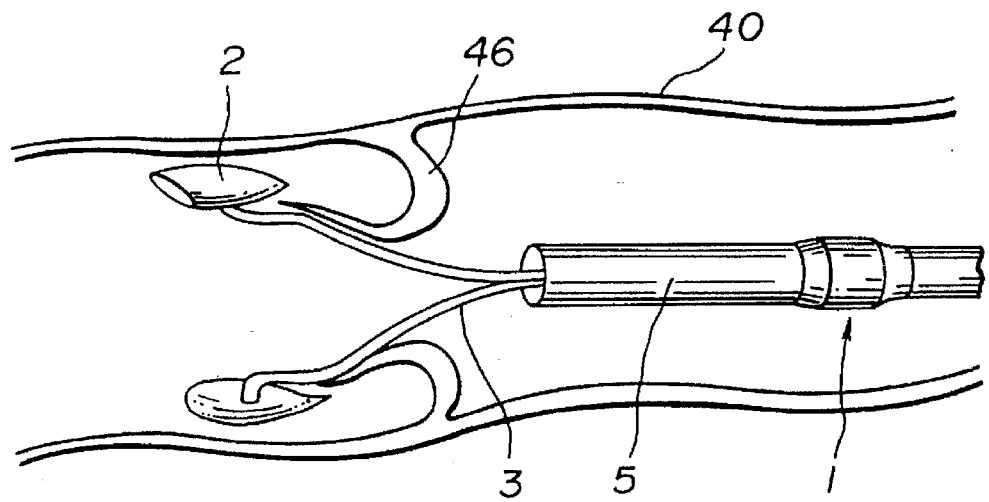
Figure 13A:
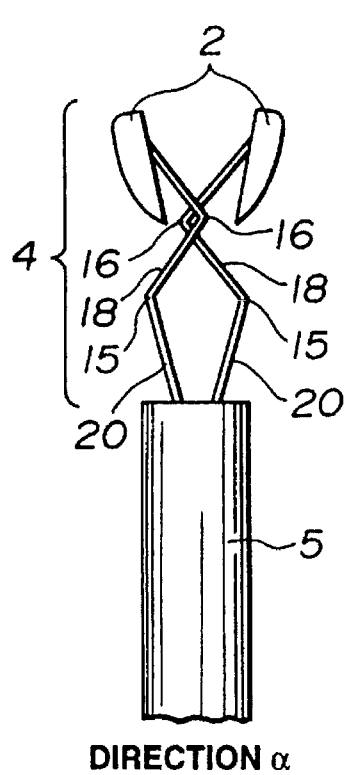
FIG. 13A is a side view in which a scene that arms have just been withdrawn is seen in a direction α.
Figure 13B:
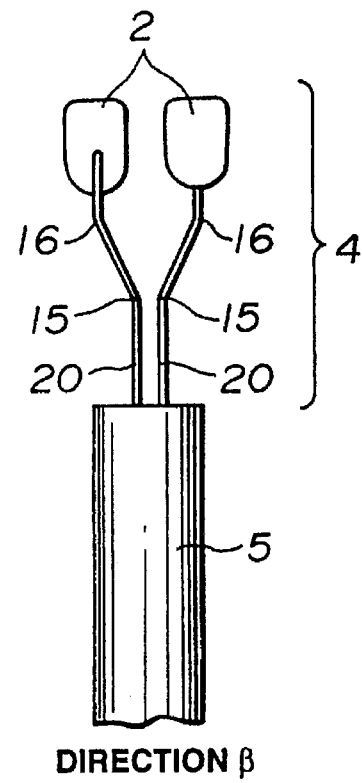
FIG. 13B is a side view in which a scene that arms have just been withdrawn is seen in a direction β.
Figure 14:
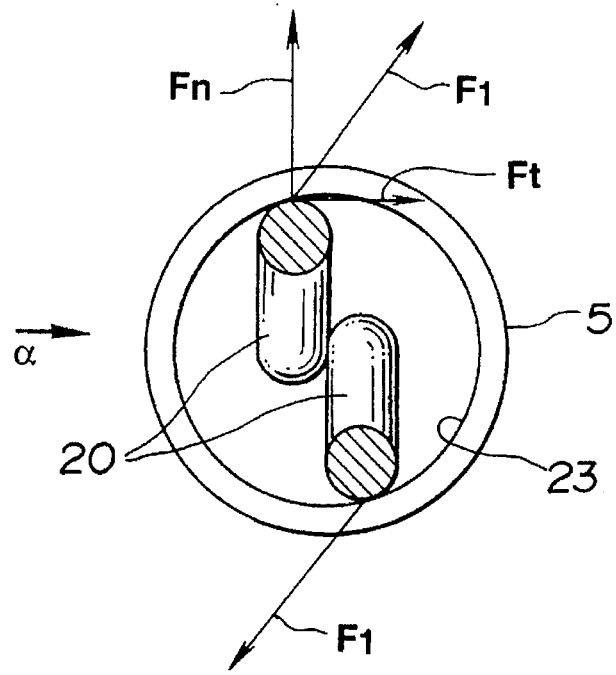
Figure 15:
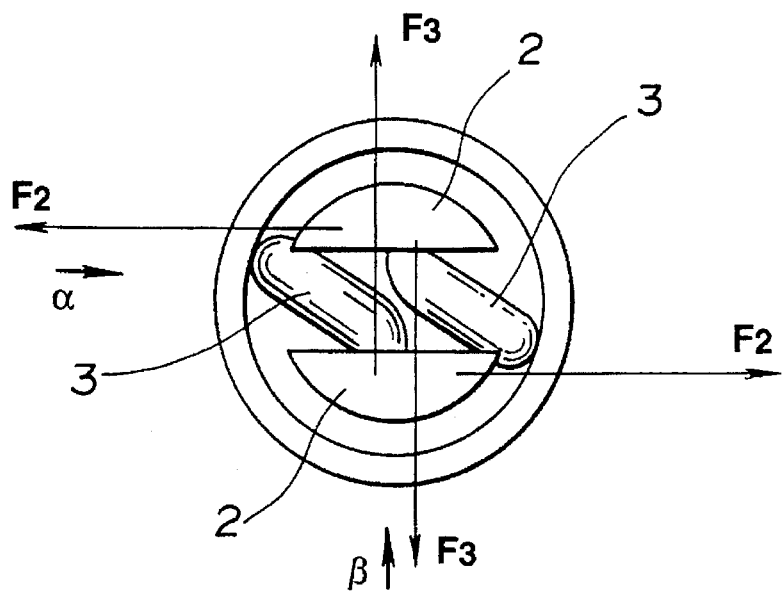

FIGS. 1 to 15 relate to the first embodiment of the present invention. FIG. 1 shows an overall configuration of a valvulotome. FIG. 2A is a lateral sectional view showing a valvulotome in a direction α. FIG. 2B is an arrow-β view of FIG. 2A. FIG. 3 is a side view showing a structure of arms. FIG. 4 is a lateral sectional view showing coupling of an arm with a cutter. FIG. 5 is a top view showing a cutter coupled with an arm. FIG. 6 is a lateral sectional view showing another structure of an arm and a cutter. FIG. 7B is an explanatory diagram showing stowage of arms. FIG. 8 is an oblique view showing arms at an angle of about 45° with respect to a direction α or β in FIG. 2A or 2B. FIG. 9 is an oblique view showing arms at an angle of about 45° in a direction different from that in FIG. 8. FIG. 10 shows an A—A section of FIG. 7A. FIG. 11 shows the usage of a venous valve valvulotome. FIG. 12 is an explanatory diagram illustrating valvotomy of a venous valve. FIG. 13A is a side view in which a scene that arms have just been withdrawn is seen in a direction α. FIG. 13B is a side view in which a scene that arms have just been withdrawn is seen in a direction β. FIG. 14 is a cross sectional view showing the vicinity of a distal part on the scene that arms have just been withdrawn. FIG. 15 is a top view in which a scene that arms is further withdrawn is seen from the tip of a distal part.

A valvulotome 1 shown in FIG. 1 has a working part 4 composed of a pair of cutters 2 and a pair of arms 3 with the cutters 2 attached at the tips thereof. The valvulotome 1 includes a distal part 5 for stowing the working part 4 that can freely advance or withdraw in an axial direction, a sheath 6 being coupled to the proximal end of the distal part 5 and possessing flexibility, and an operating part 7 coupled to the proximal end of the sheath 6. These components 5, 6, and 7 constitute an armor.

The pair of arms 3 constituting the working part 4 are formed with elastic members so that they spread outside.

With axial advancement or withdrawal, the pair of arms 3 project from the distal part 5 so as to open out, or sink into the distal part 5. The pair of arms 3 extend as shown in FIGS. 2A and 3 so as to serve as an operating wire 10. The operating wire 10 may be made of a single wire. In this embodiment, the operating wire 10 is made by twisting two wires 11. Conversely, the two wires 11 are twisted to serve as the single operating wire 10 and untwisted to serve as the pair of arms 3 at the distal portions thereof.

The arms 3 and operating wire 10 may not be united together but may be constructed independently. When constructed independently, the arms 3 and operating wire 10 should be provided with, for example, fitting sections so that they can be coupled with each other firmly.

The operating part 7 consists of a body member 8 that is coupled with the proximal end of the sheath 6 and a slider 9 that slides through the body member 8 so as to advance or withdraw freely.

As shown in FIG. 2A, the body member 8 is substantially tubulous. A plurality of ditches are formed along the external circumference of the body member in order to ensure slip-free grip. The slider 9 is composed of a sliding member 9a that is substantially tubulous, and a grip end member 9b shaped like a cylinder and engaged with the proximal end of the sliding member 9a.

The sliding member 9a has, similarly to the body member 8 a plurality of ditches along the circumference thereof. The backmost end of the operating wire 10 is stowed in a hole 9c formed in the center of the grip end member 9b. The backmost end of the operating wire 10 is stowed in the hole 9c while being folded back, and secured with an adhesive.

The sliding member 9a of the slider 9 is held in a through hole of the body member 8 so that it can slide freely. An O ring 12 is interposed between the body member 8a and the sliding member 9a of the slider 9 so that the O ring 12 yields resistance against sliding.

As shown in FIG. 2A, the operating wire 10 lies through the operating part 7 composed of the slider 9 and body member 8, the sheath 6, and the proximal half of the distal part 5. The pair of arms 3 branching out from the operating wire 10 lies through the distal half of the distal part 5.

The slider 9 is coupled with the cutters 2 via the operating wire 10 and the arms 3 forming the working part 4. When the slider 9 is advanced or withdrawn in an axial direction, the cutters 2 attached to the tips of the arms 3 advance or withdraw in the axial direction.

Next, the junctions between the arms 3 and cutters 2 will be described in conjunction with FIGS. 2A and 4 to 6. The shapes of the arms 3 will be described with reference to FIGS. 2A, 2B, and 8 to 10.

As shown in FIG. 4, the tip of each arm 3 is shaped like a ball 13 whose diameter is larger than that of the wire of the arm 3 by performing plasma heating. The ball 13 of the arm 3 is fitted into a hole 31 bored in the vicinity of the tip of each cutter 2, and immobilized therein.

Each cutter 2 has one surface flattened. When viewed from the tip thereof, the cutter 2 is stepped up. The step-up section is a stem 35. The cutter 2 has a blade 34 formed along the flat edge of the cutter 2 toward the back end thereof.

The hole 31 is bored in the stem 35 of each cutter 2. The hole 31 of the cutter 2 is composed of an idle hole 31a through which the ball 13 of the arm 3 can pass easily, and a fitting hole 31b into which the ball 13 is fitted. Note that the idle hole means a hole having a larger diameter than an object to be passed through the hole. As shown in FIG. 5 that is a top view of FIG. 4, the idle hole 31a of the hole 31 is elongated in an axial direction. Alternatively, the idle hole 31a may be elongated perpendicularly to the axial direction.

The distal portion of the idle hole 31a has a larger diameter than the ball 13 of the arm 3. The fitting hole 31b has a slightly larger diameter than the wire of the arm 3, through which the ball 13 cannot pass. For coupling the arm 3 with the cutter 2, the ball 13 of the arm 3 is passed through the idle hole 31a, and then moved to the fitting hole 31b for immobilization. For securing the arm 3 and cutter 2, after they are coupled with each other and immobilized, they are brazed firmly by filling the hole 31 with wax.

According to the foregoing structure, the arms 3 and cutters 2 are immobilized mutually. In addition to the structure that serves as a primary securing means, a secondary securing means such as brazing is employed as a further securing means in an effort to prevent the cutters 2 from coming off from the arms 3.

As shown in FIG. 6, a hole 32 and a ditch 33 may be formed in each cutter 2. Each arm 3 is cranked, the tip of the arm 3 is trapped in the ditch 33, and then the arm 3 is brazed by filling the hole 32 with wax. Thus, the arm may be coupled and secured with the cutter 2.

In either of the foregoing structures, after brazing is completed, outer surfaces 2a of the cutters 2 are smoothened by filing or buffing in order to remove oozing wax.

The arms 3 have, as shown in FIG. 2A, a structure described below. Specifically, the pair of arms 3 extending from a point at which they branch out of the operating wire 10 have the proximal halves thereof lying in parallel with each other. The pair of arms 3 have the distal halves thereof opening out at a predetermined angle. Furthermore, the arms 3 have first to third bents 15 to 17 in that order toward the tips thereof. The pair of arms 3 include first parallel opening sections 18 extending from the first bents 15 to the second bents 16, and second parallel opening sections 19 extending from the second bents 16 to third bents 17.

The portions of the pair of arms 3 extending from the point at which they branch out to the first bents 15 are, as shown in FIG. 7A, provided as bow-like arching sections 20. The portions of the arms 3 lying in parallel with each other are bifurcate sections 21.

The arms 3 have the third bents 17 in the vicinities of the tips. At the third bent 17, the arms 3 are bent at an acute angle, for example, about 90°. The tips of the arms 3 are fixed substantially perpendicularly to the respective cutters 2. Thus, the portions of the arms 3 extending between the second bents 16 and third bents 17; that is, the second parallel opening sections 19 retain gaps, which are required to trap an object to be dissected, relative to the cutters 2.

The arms 3 have the first parallel opening sections 18 extending from the second bents 16 to the first bents 15. In the first parallel opening sections 18, the arms 3 are substantially or perfectly in parallel with the blades 34 formed along the back edges of the cutters 2.

Next, the shapes of each arm 3 before and after the first bent 15, second bent, and third bent will be described with reference to FIGS. 2A and 2B.

FIG. 2A is an arrow-α view. In contrast, FIG. 2B is an arrow-β view, which is angled substantially 90° or 270° with respect to FIG. 2A. FIG. 2B is a side view of the working part 4.

As mentioned above the first bents 15 are interposed between the first parallel opening sections 18 and bow-like arching sections 20. At the first bents 15, as shown in FIG. 2A, the pair of arms 3 that are opening out are bent to lie substantially in parallel with each other. As shown in FIG. 2B, the arms 3 are bent to open out outward at a predetermined angle in directions, for example, perpendicular to the direction in which they are in parallel with each other. The direction in which the arms 3 are bent so that they are seen opening out in the direction is, for example, a direction perpendicularly to the flat surfaces of the cutters (or the directions in which the arms 3 open out).

At the second bents 16, the second parallel opening sections 19 that are the distal portions of the arms 3 are bent inward so that when the working part 4 is seen in a direction β or as illustrated in FIG. 2B, the second parallel opening sections 19 lie in parallel with each other with a predetermined gap between them. Furthermore, the second parallel opening sections 19 that are the distal portions of the arms 3 are bent at the second bents 16 so that when the working part 4 is seen in the direction α or as illustrated in FIG. 2A, the second parallel opening sections 19 open out outward at a predetermined angle in directions perpendicular to the direction in which the second parallel opening sections 19 are seen lying in parallel with each other in the direction β. The direction in which the second parallel opening sections 19 are bent so that they are seen opening out in the direction α is a direction, for example, parallel with the flat surfaces of the cutters (or directions in which the arms open out).

On the other hand, the proximal portions of the arms beyond the first bents 15 that are terminals of the first parallel opening sections 18 are the bow-like arching sections 20 that are approaching gradually. The bow-like arching sections 20 are formed so that when seen from the side shown in FIG. 2A, they open out, but that when seen from the side shown in FIG. 2B, they stay substantially in parallel with each other.

The proximal ends of the bow-like arching sections 20 lead to the operating wire 10 via the bifurcate sections 21. At the tips of the bifurcate sections 21, as shown in FIG. 10 that is an A—A sectional view of FIG. 7A, the arms 3 are arranged symmetrically with respect to the center line in the axial direction of the valvulotome 1.

The bow-like arching sections 20 open out as shown in FIG. 7A, at a maximum open angle θ when the pair of arms 3 are projected to the greatest extent. The bifurcate sections 21 terminate twist of two wires 11. For preventing the twisted wires from being untwisted in the distal part 5, it is preferred that brazing is performed to create a seal 22.

FIGS. 8 and 9 are oblique views showing the arms 3 at about 45° with respect to the directions α and β in FIG. 2A and 2B.

Next, the structure of the distal part 5 will be described. As shown in FIG. 7B, when the cutters 2 are closed or the arms 3 are pulled toward a user's hand, the pair of cutters 2 overlap and at least the blades 34 along the back edges of the cutters 2 are stowed in an opening 23 of the distal part 5. The opening 23 has a sufficiently large diameter. The opening 23 in the distal part 5 is tapered, as shown in FIG. 7A, so that the opening 23 has the largest diameter at the tip of the distal part 5. This helps the arms 3 slide freely through the opening 23. Alternatively, the opening 23 of the distal part 5 may be formed to stow the cutters 2 entirely.

With the advance or withdrawal of the slider 9, the cutters 2 and arms 3 of the valvulotome 1 are projected from the distal part 5 or the cutters 2 are stowed in the opening 23.

The blades 34 of the pair of cutters 2 are formed by the sides of the arms 3. In the course of stowing the cutters 2 or on any other occasion, unlike when the blades 34 are formed on the opposite sides of the cutters, nothing will be cut accidentally.

The operation of this embodiment will be described in conjunction with FIGS. 11 and 12 on the assumption that a venous valve is dissected.

As shown in FIG. 11, catheters 43 and 44 are inserted through a superior orifice 41 and an inferior orifice 42 which are bored in the venous duct 40. The valvulotome 1 is inserted to the venous duct 40 along the catheter 43 through the superior orifice 41.

At this time, the cutters 2 of the valvulotome 1 are closed, and the blades 19 are fully stowed in the distal part 5.

An observation means such as a fiberscope 45 is inserted along the catheter 44 through the inferior orifice 42.

In actual valvotomy, as shown in FIG. 12, when the cutters 2 approach an intended venous valve 46, the slider 9 of the operating part 7 is pushed in order to open the cutters 2. By controlling the pushed length of the slider 9, the open width between the opening cutters can be adjusted.

With the cutters 2 open, the valvulotome 1 is pulled toward the superior orifice 41 and the blades 34 formed along the back edges of the cutters 2 are hooked by the venous valve 46. Thus, the venous valve 46 is dissected. The dissection is performed under the direction observation through the foregoing observation means.

After the dissection is completed, the slider 9 is pulled toward a user's hand so that the blades are stowed in the distal part 5. The valvulotome is then removed from the vessel.

Next, the mechanism of reliably stowing the pair of cutters 2 in the distal part 5, which is an object of the present invention, will be described in conjunction with FIGS. 10 to 15.

FIG. 13A shows the working part 4 in a direction (α) perpendicular to a plane on which the pair of cutters 2 open out. FIG. 13B shows the working part 4 in a direction (β) in parallel with the plane.

Assuming that the arms 3 are slightly pulled into the distal part 5, when the arms 3 are seen in the direction α, the second bents 16 intersect. When the arms 3 in this state are seen in the direction β, since the second bents 16 are bent to stay outside the first bents 15, even if the arms 3 are pulled in as they are, the arms 3 will not get entangled.

When the arms 3 in the state shown in FIG. 13A are further pulled into the distal part 5 as shown in FIG. 14 that is a cross-sectional view of the vicinity of the tip of the distal part 5, the open angle between the bow-like arching sections 20 becomes smaller than the value θ. In other words, the bow-like arching sections 20 abut on the inner wall of the opening 23 of the distal part 5 and thereby exert outgoing forces Fn. Since the two arms 3 are located slightly off the center axis, one of the arms 3 also exerts a force Ft oriented to the center axis (to the right in FIG. 14). The one arm 3 therefore has a force F1 resulting from the combination of the outgoing force Fn and force Ft. Likewise, the other arm 3 exerts, as shown in FIG. 14, a force F1. Thus, the pair of arms 3 have parts of the bow-like arching sections 20 in contact with the opening 23 of the distal part 5 all the time, and receive a resistance that is of the same size as the force F1 but oriented in the opposite direction.

When the two arms 3 are further pulled in, as shown in FIG. 13B, the portions of the arms 3 distal to the first bents 15, which are opening out, abut on the inner wall of the opening 23 of the distal part. A force F2 is then exerted as a resistance of the inner wall toward allowing the two cutters 2 to meet. Meanwhile, as the arms 3 are being pulled in, a force is applied to a plane shown in the arrow-α view of FIG. 13A. The first bents 15 are stowed in the opening 23, and the open angle between the bow-like arching sections 20 is narrowed. The gap between the first parallel opening sections 18 shown in FIG. 7A is also narrowed. Consequently, as shown in FIG. 15, a force F3 causing the two cutters 2 to join is exerted. Thus, when the arms 3 are stowed in the opening 23, a force oriented to the center develops depending on the shapes of the arms 3. The two cutters 2 are closed and stowed in the opening 23 easily.

The force F2 works substantially perpendicularly to directions in which the cutters 2 open out. When the cutters 2 are seen from above, the force F2 causes the flat surfaces of the cutters 2 to rub together. The force F3 works in the directions in which the cutters 2 open out. When the cutters 2 are seen from above, the force F3 causes the elongated cutters 2 to join like a pair of shells. Since the arms 3 are open, in reality, as the arms 3 are being pulled in, the directions in which the forces work vary gradually. Eventually, the cutters 2 are forced to meet while rotating.

Supposing the arms 3 had, as indicated with alternate long and two short dashes lines in FIG. 2B, straight outlines in the direction β, only the forces F1 and F3 would work. The cutters 2 therefore interfere with each other and may not close successfully. A force works to narrow the open angle between the bow-like arching sections shown in FIG. 2A, causing the cutters 2 to overlap. The arms 3 may get entangled, and the cutters 2 may be stowed unsuccessfully.

In this embodiment, as described previously, the arms 3 are formed to have bents. When the cutters 2 are stowed, a resistance that occurs as a reaction against the force F1 causing the cutters 2 to stay at predetermined positions, as well as the forces F2 and F3 are exerted. In this embodiment, therefore, the two cutters 2 can be stowed in the distal part 5 reliably.

Supposing a force were exerted to cause the cutters 2 to approach too closely, since the first parallel opening sections 18 of the arms 3 cross and abut on each other, the cutters 2 will not further approach each other. The arms 3 and cutters 2 will therefore not get entangled.

Owing to the aforesaid mechanism, even if the arms 3 are bent slightly differently from they should be, the cutters 2 can be stowed reliably. This means that the arms can be molded easily. In other words, bending can be achieved through simple work. Assuming that the cutters 2 are slightly deformed due to repeated use, the blades 34 of the cutters 2 can be stowed reliably.

Figure 16:
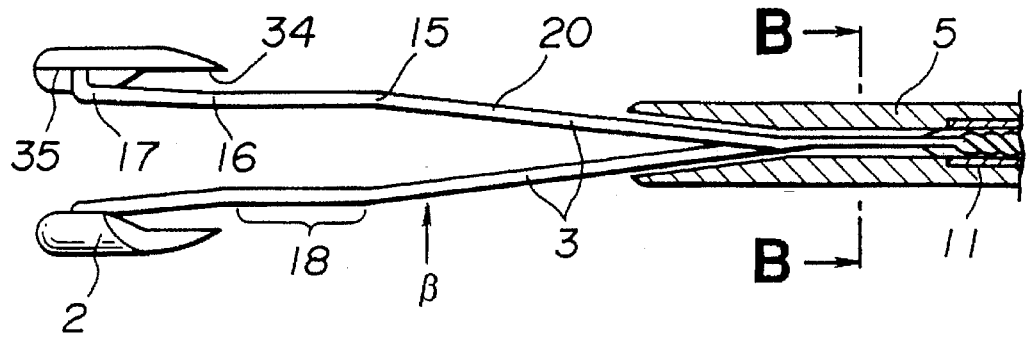
FIGS. 16 to 18 relate to the second embodiment.
Figure 17:
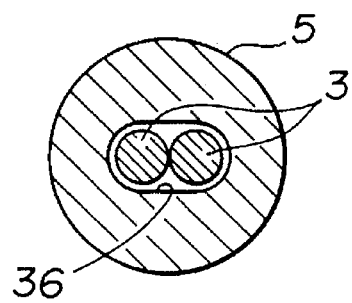
Figure 18:
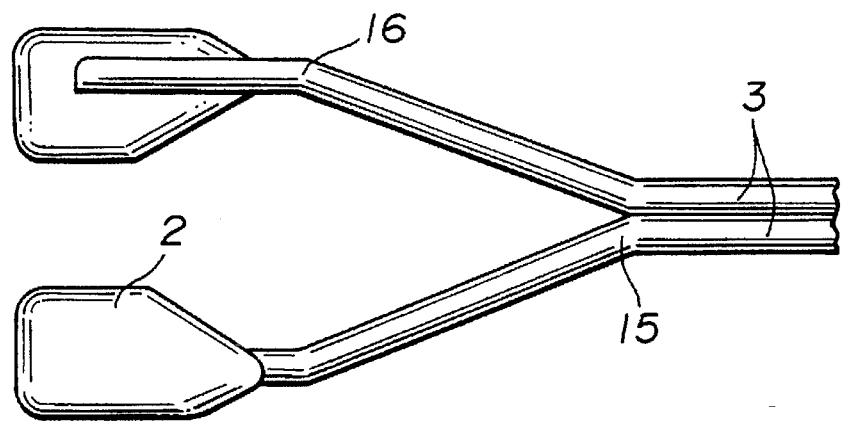

FIGS. 16 and 18 relate to the second embodiment. FIG. 16 is a longitudinal sectional view of the distal portion of a valvulotome. FIG. 17 shows a B—B section of FIG. 16. FIG. 18 is an arrow-β view of FIG. 16.

In a valvulotome of this embodiment, a section of a hollow 36 of the distal part 5 is not circular but elliptic as shown in FIG. 17. This is the only difference from the first embodiment. Components identical to those in the first embodiment will bear the same reference numerals. No mention will be made of the components and the operation identical to that of the first embodiment.

According to the present invention, with the advance or withdrawal of the operating wire, the arms project from or sink into the armor. The cutters attached to the tips of the arms open and close. When projecting from the armor, the two arms open out to stay due to the pluralities of bents so that the two cutters have a certain gap between them. The arms have such a bent that causes the two cutters to have a certain gap in a direction perpendicular to the direction in which the cutters open out. Therefore, when the two arms are pulled into the armor, forces work in directions which are dependent on the shapes of the two arms having the pluralities of bents and in which the two cutters will join. The forces include a force in a direction in which the open angle between the bow-like arching sections is narrowed, and a force in a direction perpendicular to the direction in which the open angle is narrowed. Since two forces work on the two cutters, the blades of the two cutters can be stowed in the armor reliably. Assuming that the cutters may be molded to have angles slightly different from a predetermined angle or deformed due to repeated use, the blades of the cutters can be stowed reliably.

In this embodiment, the two arms 3 are advanced or withdrawn through the elliptic hole 36. The directions in which the arms 3 projects are therefore constant. Moreover, the stowage of the cutters 2 is achieved on a stable basis. The other components and the operation and advantages are identical to those of the first embodiment, of which description will be omitted.

Figure 19:
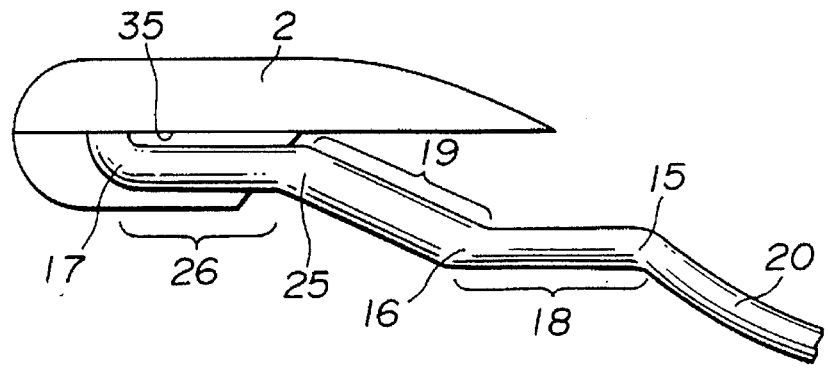
FIG. 19 shows a structure of a distal part of a valvulotome in accordance with the third embodiment of the present invention.
Figure 20:
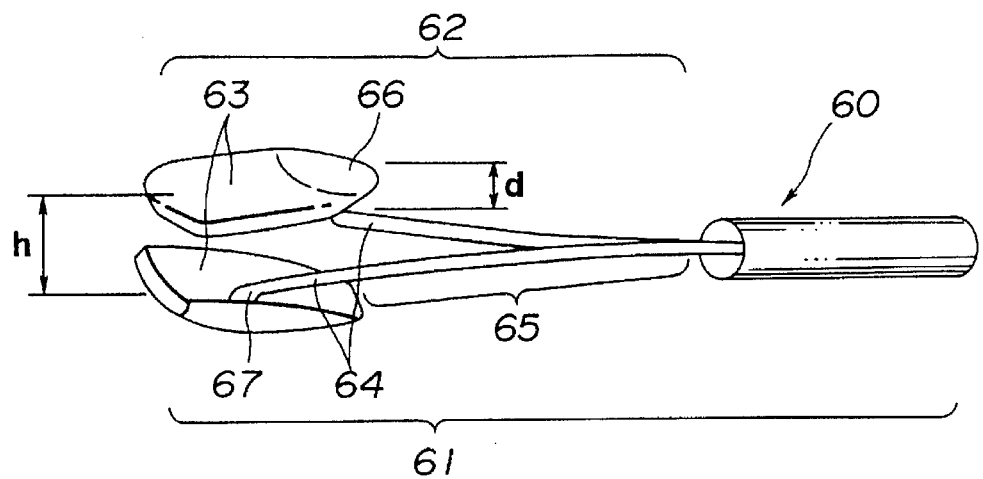
FIG. 20 shows a structure of a valvulotome in accordance with a prior art.
Figure 21:
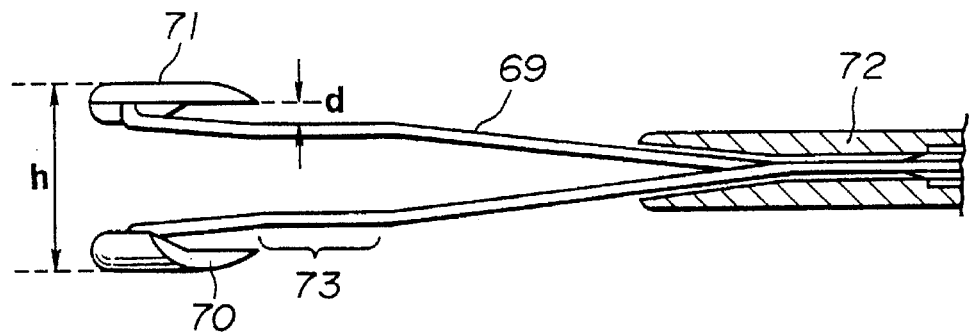
FIG. 21 shows a structure of a distal part of a valvulotome in accordance with a related art.

FIG. 19 shows a structure of the distal portion of a valvulotome in accordance with the third embodiment of the present invention.

In the third embodiment, the pair of arms 3 are bent differently and have more bents. This is the only difference from the first embodiment. The components and operation of the third embodiment are identical to those of the first embodiment. The components are assigned the same reference numerals, of which description will be omitted. The distal portion of a valvulotome are not illustrated.

The pair of arms 3 have fourth bents between the second bents 16 and third bents 17. The portions of the arms 3 between the second bents 16 and fourth bents 25 are provided as the second parallel opening sections 19. The portions of the arms 3 between the second bents 16 and fourth bents 25 are provided as the second parallel opening sections 19. The portions of the arms 3 between the fourth bents 25 and the third bents 17 are provided as second parallel sections 26 that lie in parallel with the stems 35 of the cutters 2.

It can be said that the valvulotome of this embodiment has higher durability than the one of the first embodiment. The other operation and advantages are identical to those of the first embodiment, of which description will be omitted.

In the present invention, it will be apparent that a wide range of different working modes can be formed on the basis of the spirit of the invention. This invention will be limited to the appended claims but not be restricted to any specific working modes.

What is claimed is:

1. A freely projectable/sinkable valvulotome, comprising:
   an armor;
   an operating wire lying in said armor so as to advance or withdraw freely and having the distal portion thereof bifurcating into two arms; and
   two cutters attached to tips of said two arms, said cutters having blades,
   wherein at least parts of said two cutters and said two arms are capable of projecting from or sinking into said armor when said operating wire is advanced or withdrawn;
   wherein said two arms have a plurality of bents so that when said arms project, said two cutters open at a predetermined angle in different directions, and so that when said arms are stowed in said armor, forces exerted from said armor change directions with said plurality of bents as boundaries, and
   wherein said two arms include:
      first opening sections formed to open out from bifurcated sections of said arms so that said cutters open out at a predetermined angle,
      second opening sections formed as portions of said arms distal to said first opening sections, formed to lie in parallel with each other in a direction in which said first opening sections open out, and formed to open out in directions perpendicular to said direction in which said first opening sections open out so that said cutters lie outside an outer diameter of said armor but do not interfere with each other,
      third opening sections formed as portions of said arms distal to said second opening sections, and formed to open out at a predetermined angle in directions substantially identical to said directions in which said first opening sections open out so that when said first opening sections are stowed in said armor, at least edges of said pair of cutters are oriented into said armor, and
      junctions formed as portions of said arms distal to said third opening sections, and designed to couple said cutters so that when said first opening sections project from said armor, said pair of cutters lie in parallel with each other, and
   wherein said armor is a substantially hollow member which accommodates therein said operating wire and at least parts of said arms, and wherein said substantially hollow member accommodates therein said at least parts of said cutters when said operating wire is withdrawn.

2. A freely projectable/sinkable valvulotome according to claim 1, wherein at least portions of said blades of said two cutters are capable of being stowed in said armor.

3. A freely projectable/sinkable valvulotome, comprising:
   an armor;
   an operating wire lying in said armor so as to advance or withdraw freely and having the distal portion thereof bifurcating into two arms; and
   two cutters attached to tips of said two arms, said cutters having blades,
   wherein at least parts of said two cutters and said two arms project from or sink into said armor when said operating wire is advanced or withdrawn, wherein said two arms are formed to open out gradually toward the tips thereof so that as said arms are being stowed in said armor, forces deriving from contact with said armor work toward causing said two cutters at the tips thereof to join, wherein said two arms have a plurality of bents, which allow directions in which said arms open out to change sequentially toward the tips of said arms in intermediate portions thereof so that as said two arms are being stowed in said armor, said forces causing said two cutters to join change directions with said bents as boundaries, and wherein said two arms include:
- first opening sections formed to open out from bifurcated sections of said arms so that said cutters open out at a predetermined angle,
- second opening sections formed as portions of said arms distal to said first opening sections, formed to lie in parallel with each other in a direction in which said first opening sections open out, and formed to open out in directions perpendicular to said direction in which said first opening sections open out so that said cutters lie outside an outer diameter of said armor but do not interfere with each other,
- third opening sections formed as portions of said arms distal to said second opening sections, and formed to open out at a predetermined angle in directions substantially identical to said directions in which said first opening sections open out so that when said first opening sections are stowed in said armor, at least edges of said pair of cutters are oriented into said armor, and
- junctions formed as portions of said arms distal to said third opening sections, and designed to couple said cutters so that when said first opening sections project from said armor, said pair of cutters lie in parallel with each other, and wherein said armor is a substantially hollow member which accommodates therein said operating wire and at least parts of said arms, and wherein said substantially hollow member accommodates therein said at least parts of said cutters when said operating wire is withdrawn.

4. A freely projectable/sinkable valvulotome according to claim 3, wherein said operating wire is made by braiding two wires, and said wires branch out as said arms.

5. A freely projectable/sinkable valvulotome according to claim 3, wherein said armor has a hollow whose section is elliptic or oval, and said arms are stowed in said hollow so that they lie in parallel with each other and stay closely or in contact with each other.

6. A freely projectable/sinkable valvulotome according to claim 5, wherein said two arms have substantially circular sections.

7. A freely projectable/sinkable valvulotome according to claim 3, wherein said armor has a distal opening, which serves as an opening through which said two arms project or sink, at the tips thereof, and wherein said distal opening is tapered to become wider toward the tips thereof so that at least ends of said blades of said two cutters opposed to said armor are stowed in said armor.

8. A freely projectable/sinkable valvulotome according to claim 3, wherein said two arms are formed so that said forces applied to said arms, when said arms are being withdrawn into said armor, change directions substantially perpendicularly with any of said plurality of bents as boundaries.

9. A freely projectable/sinkable valvulotome according to claim 8, wherein said two arms are formed so that said forces applied to said arms change between a direction in parallel with said blades of said two cutters and a direction perpendicular to the direction.

10. A freely projectable/sinkable valvulotome according to claim 3, wherein the portions of said two arms between one of said bents and other ones of said bents are formed so that when seen from one side oriented in a first direction, said arms lie in parallel with each other, and so that when seen from another side oriented in a second direction that is different from said second direction, said arms open out with a predetermined open angle therebetween.

11. A freely projectable/sinkable valvulotome according to claim 10, wherein said direction in which said one side is oriented is a direction substantially perpendicular to directions in which said cutters open out, and said direction different from said direction in which said one side is oriented is a direction substantially in parallel with the directions in which said cutters open out.

12. A freely projectable/sinkable valvulotome according to claim 10, wherein said two cutters have one surfaces flattened; and wherein said direction in which said one side is oriented is a direction substantially perpendicular to said flat surfaces of said cutters, and said direction different from said direction in which said one side is oriented is a direction substantially in parallel with said flat surfaces of said cutters.

13. A freely projectable/sinkable valvulotome according to claim 3, wherein when seen from one side, the portions of said two arms between certain (one) bents and another bents are in parallel with each other, and when seen from another side oriented in direction that is different by a predetermined angle from said direction in which said one side is oriented, said portions of said arms open out with a predetermined open angle between them.

14. A freely projectable/sinkable valvulotome according to claim 3, wherein said predetermined angle by which said another side is displaced from said one side is 90° or 270° with respect to said direction in which said one side is oriented.

15. A freely projectable/sinkable valvulotome according to claim 3, wherein said two arms have first bents, which allow said directions in which said arms open out to change gradually toward the tips of said arms, in the middles of thereof, and also have second bents, which allow said directions in which said arms open out to further change, in the portions thereof distal to said first bents, so that as said two arms are being stowed in said armor, said forces causing said two cutters to join change directions with said first bents and second bents as boundaries.

16. A freely projectable/sinkable valvulotome according to claim 15, wherein said two arms has third bents near the tips thereof so that a predetermined gap is retained between said blades of said cutters attached to the tips of said arms and said arms.

17. A freely projectable/sinkable valvulotome according to claim 15, wherein the portions of said two arms between said first bents and said second bents are formed so that when seen from one side, said arms lie in parallel with each other, and so that when seen from another side oriented in a direction that is different substantially by a predetermined angle from the direction in which said one side is oriented, said arms open out at a predetermined angle.

18. A freely projectable/sinkable valvulotome according to claim 17, wherein said predetermined angle by which said another side is displaced from said one side is 90° or 270° with respect to said direction in which said one side is oriented.

19. A freely projectable/sinkable valvulotome according to claim 17, wherein said two arms have third bents near the tips thereof so that a predetermined gap is retained between said blades of said cutters attached to the tips of said arms and said arms, and so that when seen from said one side, said blades of said cutters lie in parallel with said parallel portions of said arms.

20. A freely projectable/sinkable valvulotome according to claim 17, wherein said two arms have third bents near the tips thereof so that a predetermined gap is retained between said blades of said cutters attached to the tips of said arms and said arms; and wherein the portions of said two arms between said second bents and third bents are formed so that when seen from another side different from said one side, from which said portions of said arms between said first bents and said second bents are seen lying in parallel with each other, said arms lie in parallel with one another, and so that when seen from yet another side oriented in a direction that is different by a predetermined angle from said direction in which said another side different from said one side is oriented, said arms open out with a predetermined open angle between them.

21. A freely projectable/sinkable valvulotome according to claim 17, wherein said one side is displaced by 90° or 270° from said another side, and said yet another side is displaced by 90° or 270° that is provided as said predetermined angle.

22. A freely projectable/sinkable valvulotome according to claim 20 or 21, wherein said one side, form which said portions of said arms between said first bents and said second bents are seen lying in parallel with each other, is displaced substantially by 90° from said another side different from said one side.

23. A freely projectable/sinkable valvulotome, comprising:
an armor;
an operating wire lying in said armor so as to advance or withdraw freely, said operating wire having the distal portion thereof bifurcating into two arms; and
a pair of cutters attached to tips of said arms which branch out, said cutters having blades with edges that are opposed to the distal end of said armor,
wherein said pair of arms include:
first opening sections formed to open out from bifurcated sections of said arms so that said pair of cutters open out at a predetermined angle,
second opening sections formed as portions of said arms distal to said first opening sections, formed to lie in parallel with each other in a direction in which said first opening sections open out, and formed to open out in directions perpendicular to said direction in which said first opening sections open out so that said pair of cutters lie outside an outer diameter of said armor but do not interfere with each other,
third opening sections formed as portions of said arms distal to said second opening sections, and formed to open out at a predetermined angle in directions substantially identical to said directions in which said first opening sections open out so that when said first opening sections are stowed in said armor, at least edges of said pair of cutters are oriented into said armor, and
junctions formed as portions of said arms distal to said third opening sections, and designed to couple said pair of cutters so that when said first opening sections project from said armor, said pair of cutters lie in parallel with each other,
wherein said armor is a substantially hollow member which accommodates therein said operating wire and at least parts of said pair of arms, and wherein said substantially hollow member accommodates therein said at least parts of said pair of cutters when said operating wire is withdrawn.

24. A freely projectable/sinkable valvulotome according to claim 23, wherein said armor has an opening through which said pair of arms project or sink, and said opening is tapered so that an inner diameter thereof gets larger toward the distal end of said armor.

25. A freely projectable/sinkable valvulotome according to claim 23, wherein said pair of cutters have one surfaces flattened.

26. A venous valve valvulotome, comprising:
an armor;
an operating wire lying in said armor so as to advance or withdraw freely, said operating wire having the distal portions thereof bifurcate into two arms; and
two cutters attached to tips of said two arms and provided with blades,
wherein at least portions of said two cutters and said arms are capable of projecting from or sinking into said armor when said operating wire is advanced or withdrawn,
wherein said two arms are formed to gradually open out toward tips thereof so that as said arms are being stowed in said armor, forces due to contact with said armor work in a direction in which said two cutters attached to the tips of said arms join, wherein said two arms have a plurality of bents which allow the directions in which said arms open out to gradually change toward the tips of said arms in the intermediate portions thereof so that as said two arms are being stowed in said armor, said forces causing said two cutters to join change directions with said bents as boundaries, and
wherein said two arms include:
first opening sections formed to open out from bifurcated sections of said arms so that said cutters open out at a predetermined angle,
second opening sections formed as portions of said arms distal to said first opening sections, formed to lie in parallel with each other in a direction in which said first opening sections open out, and formed to open out in directions perpendicular to said direction in which said first opening sections open out so that said cutters lie outside an outer diameter of said armor but do not interfere with each other,
third opening sections formed as portions of said arms distal to said second opening sections, and formed to open out at a predetermined angle in directions substantially identical to said directions in which said first opening sections open out so that when said first opening sections are stowed in said armor, at least edges of said pair of cutters are oriented into said armor, and
junctions formed as portions of said arms distal to said third opening sections, and designed to couple said cutters so that when said first opening sections project from said armor, said pair of cutters lie in parallel with each other, and
wherein said armor is a substantially hollow member which accommodates therein said operating wire and at least parts of said arms, and wherein said substantially hollow member accommodates therein said at least parts of said cutters when said operating wire is withdrawn.

27. A freely projectable/sinkable valvulotome, comprising:

an armor;

an operating wire lying in said armor so as to advance or withdraw freely and having the distal portion thereof bifurcating into two arms; and two cutters attached to tips of said two arms, said cutters having blades, wherein at least parts of said two cutters and said two arms project from or sink into said armor when said operating wire is advanced or withdrawn, wherein said two arms are formed to open out gradually toward the tips thereof so that as said arms are being stowed in said armor, forces deriving from contact with said armor work toward causing said two cutters at the tips thereof to join, wherein said two arms have a plurality of bents, which allow directions in which said arms open out to change sequentially toward the tips of said arms in intermediate portions thereof so that as said two arms are being stowed in said armor, said forces causing said two cutters to join change directions with said bents as boundaries, wherein said armor is a substantially hollow member which accommodates therein said operating wire and at least parts of said two arms, and wherein said substantially hollow member accommodates therein said at least parts of said two cutters when said operating wire is withdrawn, wherein said armor has a cross-section that is elliptical or oval, and wherein said arms are stowed in said hollow member so that said arms lie in parallel with each other and stay closely or in contact with each other, and wherein said two arms have substantially circular cross-sections.

28. A freely projectable/sinkable valvulotome, comprising:

an armor;

an operating wire lying in said armor so as to advance or withdraw freely and having the distal portion thereof bifurcating into two arms; and two cutters attached to tips of said two arms, said cutters having blades, wherein at least parts of said two cutters and said two arms project from or sink into said armor when said operating wire is advanced or withdrawn, wherein said two arms are formed to open out gradually toward the tips thereof so that as said arms are being stowed in said armor, forces deriving from contact with said armor work toward causing said two cutters at the tips thereof to join, wherein said two arms have a plurality of bents, which allow directions in which said arms open out to change sequentially toward the tips of said arms in intermediate portions thereof so that as said two arms are being stowed in said armor, said forces causing said two cutters to join change directions with said bents as boundaries, wherein said armor is a substantially hollow member which accommodates therein said operating wire and at least parts of said two arms, and wherein said substantially hollow member accommodates therein said at least parts of said two cutters when said operating wire is withdrawn, and wherein the portions of said two arms between one of said bents and other ones of said bents are formed so that when seen from one side oriented in a first direction, said arms lie in parallel with each other, and so that when seen from another side oriented in a second direction that is different from said second direction, said arms open out with a predetermined open angle therebetween.

29. A freely projectable/sinkable valvulotome according to claim 28, wherein said direction in which said one side is oriented is a direction substantially perpendicular to directions in which said cutters open out, and said direction different from said direction in which said one side is oriented is a direction substantially in parallel with the directions in which said cutters open out.

30. A freely projectable/sinkable valvulotome according to claim 28, wherein said two cutters have surfaces flattened, and wherein said direction in which said one side is oriented is a direction substantially perpendicular to said flat surfaces of said cutters, and said direction different from said direction in which said one side is oriented is a direction substantially in parallel with said flat surfaces of said cutters.

31. A freely projectable/sinkable valvulotome, comprising:

an armor;

an operating wire lying in said armor so as to advance or withdraw freely and having the distal portion thereof bifurcating into two arms; and two cutters attached to tips of said two arms, said cutters having blades, wherein at least parts of said two cutters and said two arms project from or sink into said armor when said operating wire is advanced or withdrawn, wherein said two arms are formed to open out gradually toward the tips thereof so that as said arms are being stowed in said armor, forces deriving from contact with said armor work toward causing said two cutters at the tips thereof to join, wherein said two arms have a plurality of bents, which allow directions in which said arms open out to change sequentially toward the tips of said arms in intermediate portions thereof so that as said two arms are being stowed in said armor, said forces causing said two cutters to join change directions with said bents as boundaries, wherein said armor is a substantially hollow member which accommodates therein said operating wire and at least parts of said two arms, and wherein said substantially hollow member accommodates therein said at least parts of said two cutters when said operating wire is withdrawn, and wherein when seen from one side, the portions of said two arms between one of said bents and another one of said bents are in parallel with each other, and when seen from another side oriented in direction that is different by a predetermined angle from said direction in which said one side is oriented, said portions of said arms open out with a predetermined open angle therebetween.

32. A freely projectable/sinkable valvulotome according to claim 31, wherein said two arms has third bents near the tips thereof so that a predetermined gap is retained between said blades of said cutters attached to the tips of said arms and said arms.

33. A freely projectable/sinkable valvulotome according to claim 31, wherein the portions of said two arms between said first bents and said second bents are formed so that when seen from one side, said arms lie in parallel with each other, and so that when seen from another side oriented in a direction that is different substantially by a predetermined angle from the direction in which said one side is oriented, said arms open out at a predetermined angle.

34. A freely projectable/sinkable valvulotome according to claim 33, wherein said predetermined angle by which said another side is displaced from said one side is 90° or 270° with respect to said direction in which said one side is oriented.

35. A freely projectable/sinkable valvulotome according to claim 33, wherein said two arms have third bents near the tips thereof so that a predetermined gap is retained between said blades of said cutters attached to the tips of said arms and said arms, and so that when seen from said one side, said blades of said cutters lie in parallel with said parallel portions of said arms.

36. A freely projectable/sinkable valvulotome according to claim 33, wherein said two arms have third bents near the tips thereof so that a predetermined gap is retained between said blades of said cutters attached to the tips of said arms and said arms, and wherein the portions of said two arms between said second bents and third bents are formed so that when seen from another side different from said one side, from which said portions of said arms between said first bents and said second bents are seen lying in parallel with each other, said arms lie in parallel with one another, and so that when seen from yet another side oriented in a direction that is different by a predetermined angle from said direction in which said another side different from said one side is oriented, said arms open out with a predetermined open angle therebetween.

37. A freely projectable/sinkable valvulotome according to claim 33, wherein said one said is displaced by 90° or 270° from said another side, and said yet another side is displaced by 90° or 270° that is provided as said predetermined angle.

38. A freely projectable/sinkable valvulotome according to claim 36 or 37, wherein said one side, from which said portions of said arms between said first bents and said second bents are seen lying in parallel with each other, is displaced substantially by 90° from said another side different from said one side.

39. A freely projectable/sinkable valvulotome, comprising:

an armor;

an operating wire lying in said armor so as to advance or withdraw freely and having the distal portion thereof bifurcating into two arms; and two cutters attached to tips of said two arms, said cutters having blades, wherein at least parts of said two cutters and said two arms project from or sink into said armor when said operating wire is advanced or withdrawn, wherein said two arms are formed to open out gradually toward the tips thereof so that as said arms are being stowed in said armor, forces deriving from contact with said armor work toward causing said two cutters at the tips thereof to join, wherein said two arms have a plurality of bents, which allow directions in which said arms open out to change sequentially toward the tips of said arms in intermediate portions thereof so that as said two arms are being stowed in said armor, said forces causing said two cutters to join change directions with said bents as boundaries, wherein said armor is a substantially hollow member which accommodates therein said operating wire and at least parts of said two arms, and wherein said substantially hollow member accommodates therein said at least parts of said two cutters when said operating wire is withdrawn, and wherein said predetermined angle by which said another side is displaced from said one side is 90° or 270° with respect to said direction in which said one side is oriented.

40. A freely projectable/sinkable valvulotome, comprising:

an armor;

an operating wire lying in said armor so as to advance or withdraw freely and having the distal portion thereof bifurcating into two arms; and two cutters attached to tips of said two arms, said cutters having blades, wherein at least parts of said two cutters and said two arms project from or sink into said armor when said operating wire is advanced or withdrawn, wherein said two arms are formed to open out gradually toward the tips thereof so that as said arms are being stowed in said armor, forces deriving from contact with said armor work toward causing said two cutters at the tips thereof to join, wherein said two arms have a plurality of bents, which allow directions in which said arms open out to change sequentially toward the tips of said arms in intermediate portions thereof so that as said two arms are being stowed in said armor, said forces causing said two cutters to join change directions with said bents as boundaries, wherein said armor is a substantially hollow member which accommodates therein said operating wire and at least parts of said two arms, and wherein said substantially hollow member accommodates therein said at least parts of said two cutters when said operating wire is withdrawn, and wherein said two arms have first bents, which allow said directions in which said arms open out to gradually change toward the tips of said arms, in intermediate portions thereof, and also have second bents, which allow said directions in which said arms open out to further change, in the portions thereof distal to said first bents, so that as said two arms are being stowed in said armor, said forces causing said two cutters to join change directions with said first bents and second bents as boundaries.

* * * * *